(12) United States Patent
Chen et al.

(10) Patent No.: US 10,718,752 B2
(45) Date of Patent: Jul. 21, 2020

(54) PHYSIOLOGICAL PARAMETER MEASUREMENT MODULE

(71) Applicant: BIONIME CORPORATION, Taichung (TW)

(72) Inventors: Ming-Ta Chen, Taichung (TW); Tung-Liang Liu, Taichung (TW)

(73) Assignee: BIONIME CORPORATION, Taichung (TW)

( * ) Notice: Subject to any disclaimer, the term of this patent is extended or adjusted under 35 U.S.C. 154(b) by 143 days.

(21) Appl. No.: 15/701,901

(22) Filed: Sep. 12, 2017

(65) Prior Publication Data

US 2018/0074041 A1  Mar. 15, 2018

(30) Foreign Application Priority Data

Sep. 13, 2016 (TW) .............................. 105129875 A (51) Int. Cl.
  *G01N 33/49* (2006.01)
  *G01N 33/487* (2006.01)
  *G01N 27/04* (2006.01)

(52) U.S. Cl.
  CPC ............. *G01N 33/49* (2013.01); *G01N 27/04* (2013.01); *G01N 33/48771* (2013.01); *G01N 33/48785* (2013.01)

(58) Field of Classification Search
  CPC .. G01N 33/49; G01N 27/04; G01N 33/48771; G01N 33/48785; G01R 19/145; G01R 27/04; G01R 31/001
  USPC ....... 324/600, 693, 639, 459–469, 500, 663, 324/714, 719, 300, 317–322
  See application file for complete search history.

(56) References Cited

U.S. PATENT DOCUMENTS

2012/0266251 A1* 10/2012 Birtwhistle ......... G06F 19/3481
  726/26
2014/0248694 A1* 9/2014 Xu ..................... G01N 27/3272
  435/287.9

* cited by examiner

*Primary Examiner* — Melissa J Koval
*Assistant Examiner* — Trung Nguyen
(74) *Attorney, Agent, or Firm* — Volpe and Koenig, P.C.

(57) ABSTRACT

A test strip reader is disclosed. The test strip reader comprises a module main body and a circuit board. The module main body includes an upper cover, a grounding element and at least one operation hole containing a first operation movement assembly and a second operation movement assembly, wherein the upper cover and the module main body are formed integrally, and a condition of one of a contact status and a separation status between the second operation movement assembly and the grounding element determines a read signal.

13 Claims, 7 Drawing Sheets

PHYSIOLOGICAL PARAMETER MEASUREMENT MODULE

CROSS-REFERENCE TO RELATED APPLICATION AND CLAIM OF PRIORITY

The application claims the benefit of Taiwan Patent Application No. 105129875, filed on Sep. 13, 2016, at the Taiwan Intellectual Property Office, the disclosures of which are incorporated herein in their entirety by reference.

FIELD OF THE INVENTION

The present invention is related to a test strip reader, and more particularly to a test strip reader disposed in an electronic device for measuring an analyte.

BACKGROUND OF THE INVENTION

Devices for measuring physiological parameters such as blood glucose concentration, cholesterol value, uric acid concentration, or PH value can obtain samples through test strips after sample collecting to facilitate the measurement under predetermined test conditions. Some analyte measuring devices can read different types of test strips. In order for the analyte measuring device to be able to identify the type of test strips or to enable anti-counterfeiting, one may mechanically encode the test strip at a certain portion of the test strip, for example by making some coding recesses. The analyte measurement device can be used to read the test strip, and at the same time can also be used for the identification of these recesses to identify the type of test strips to assist the reading module to select the appropriate test configuration as well as enable the anti-counterfeiting function.

Figure 1:
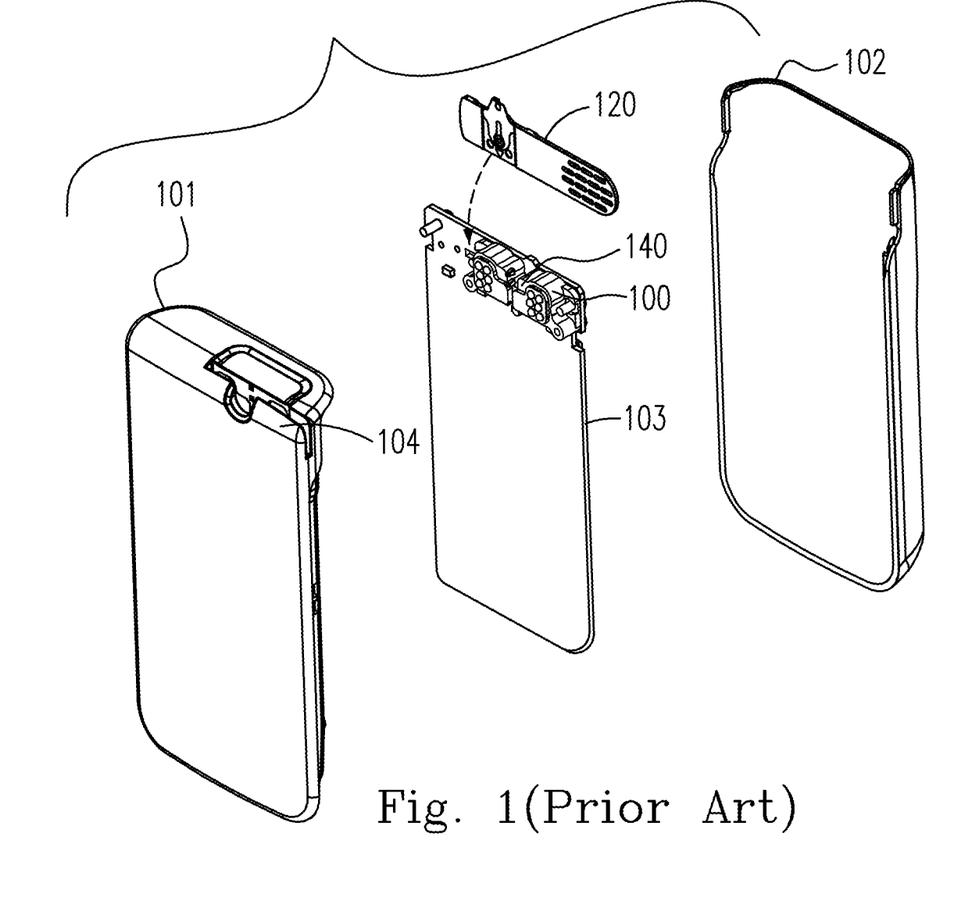
FIG. 1 is a schematic diagram showing a prior art design of a device for measuring physiological parameters.

Modules designed for mechanically readable encoding may have some practical issues concerning instrument assembly. For example, the assembly of multiple components makes dimensional tolerances difficult to control. Please refer to FIG. 1, which is a schematic diagram showing an upper cover 101 having a top structure 104 of a strip slot before assembly according to a prior art design. The space for the strip slot is formed after the circuit board 103 having a strip reader module 100 has been assembled with the upper cover 101 and a back cover 102 piece by piece. However, the distance between the strip contacting surfaces of the strip slot varies due to the tolerances control of the upper cover 101 and the strip reader module 100 disposed on the circuit board 103 during manufacturing. Eventually a reworking for adjusting the space for the strip slot is inevitable when the space is out of specification or the strip reader module 100 cannot precisely identify the code on the strip due to measurement bias.

Moreover, contamination often occurs when the reader module receives a test strip containing a blood sample. If the blood sample accidentally enters the device for measuring physiological parameters, it may cause inspection errors due to contamination or even malfunctions of electronic components. Thus, there is also a need to avoid potential contamination.

In order to overcome the drawbacks in the prior art, a novel design of a test strip reader disposed in an electronic device for measuring an analyte is required.

SUMMARY OF THE INVENTION

In accordance with one aspect of the present invention, a test strip reader is disclosed. The test strip reader comprises a module main body and a circuit board. The module main body includes an upper cover, a grounding element and at least one operation hole containing a first operation movement assembly and a second operation movement assembly, wherein the upper cover and the module main body are formed integrally, and a condition of one of a contact status and a separation status between the second operation movement assembly and the grounding element determines a read signal.

In accordance with another aspect of the present invention, a test strip reader is disclosed. The test strip reader comprises a module main body and a circuit board. The module main body includes an upper cover, a grounding element and at least one operation hole disposing therein a conducting element, wherein the upper cover and the module main body are formed integrally, and a condition of one of a contact status and a separation status between the conducting element and the grounding element determines a read signal.

In accordance with a further aspect of the present invention, an electronic device for measuring an analyte is disclosed. The electronic device comprises a test strip reader, a top cover and a back cover. The test strip reader includes an upper strip contacting surface and a lower strip contacting surface, wherein the upper strip contacting surface and the lower strip contacting surface form therebetween a space for accommodating a test strip, and the upper and lower strip contacting surfaces and the test strip reader are formed integrally. The top cover is disposed above the test strip reader and optionally shelters a top surface of the test strip reader. The back cover is disposed below the test strip reader and shelters a bottom surface of the test strip reader.

The novel design in the present invention can fully satisfy the requirements in terms of controlling the manufacturing tolerance of the strip slot as well as contamination prevention and ease of assembly. Thus, the present invention has utility for industry.

The objectives and advantages of the present invention will become more readily apparent to those ordinarily skilled in the art after reviewing the following detailed descriptions and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for the purposes of illustration and description only; they are not intended to be exhaustive or to be limited to the precise form disclosed.

Figure 2A:
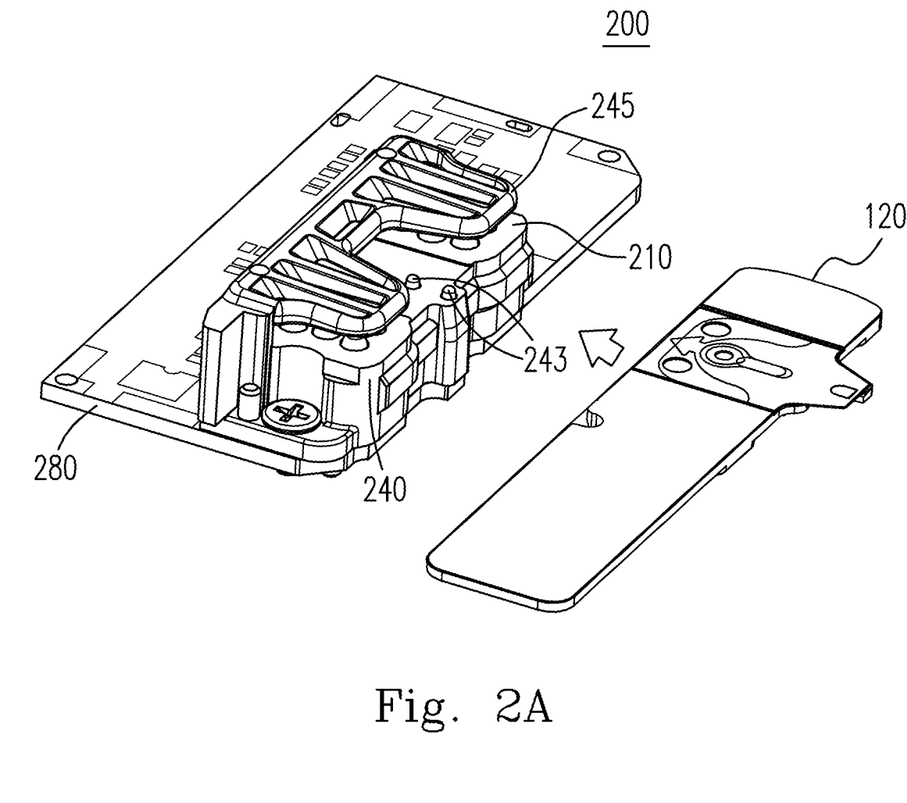
FIG. 2A is a perspective view showing a test strip reader module according to one embodiment of the present invention.

Please refer to FIG. 2A, which shows a perspective view showing a test strip reader module 200 according to one embodiment of the present invention. The test strip reader module 200 comprises a circuit board 280 and a module main body 240 disposed thereon. The module main body 240 includes an upper cover 245, and a strip insertion slot 210 is formed between the module main body 240 and the upper cover 245. The module main body 240 also includes two electrical contact portions 243 disposed at the location of the strip insertion slot 210. The two electrical contact portions 243 can be electrically connected to corresponding electrodes (not shown) on a test strip 120 when inserted into the strip insertion slot 210. Materials for the electrical contact portions 243 and the corresponding electrodes are preferably of gold material such as the material used by Rightest® blood test strip accompanied with an embedded gold electrode technology (for example, the Validus® technology) to have better stability and conductivity.

Figure 2B:
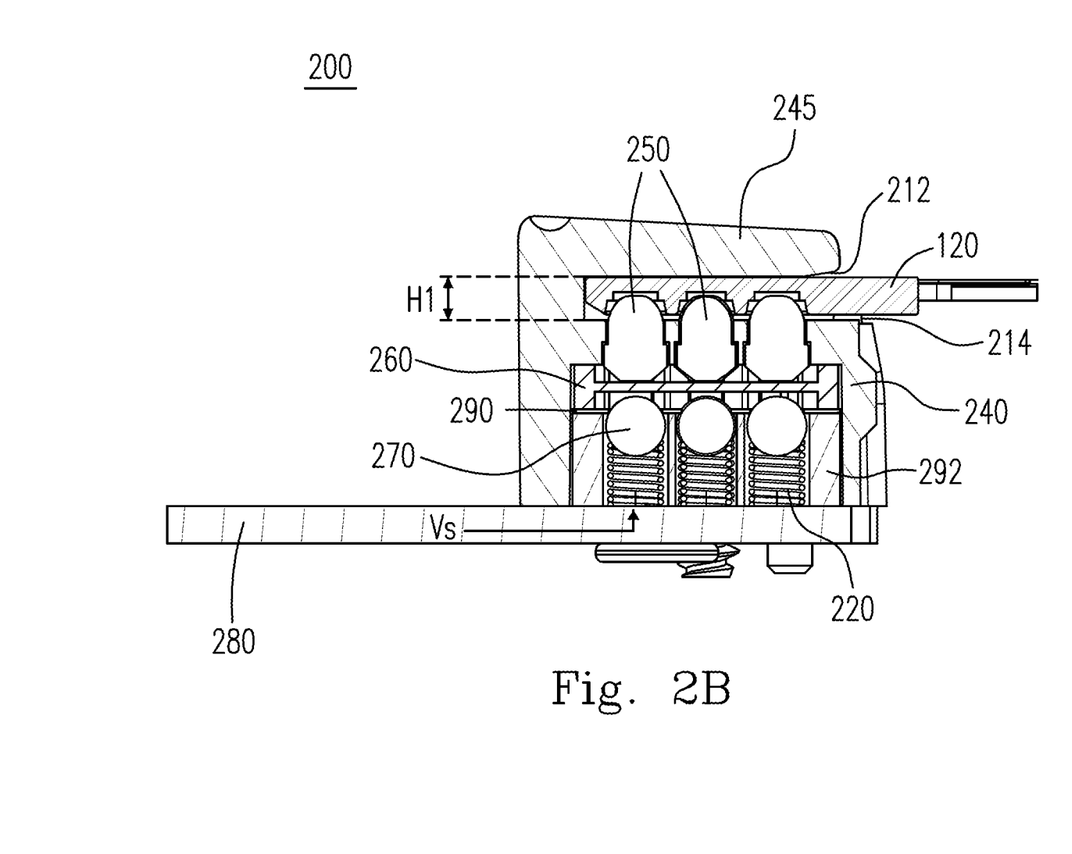
FIG. 2B-2C are schematic diagrams showing sectional views of the test strip reader module according to FIG. 2A when the strip is inserted therein.
Figure 2C:
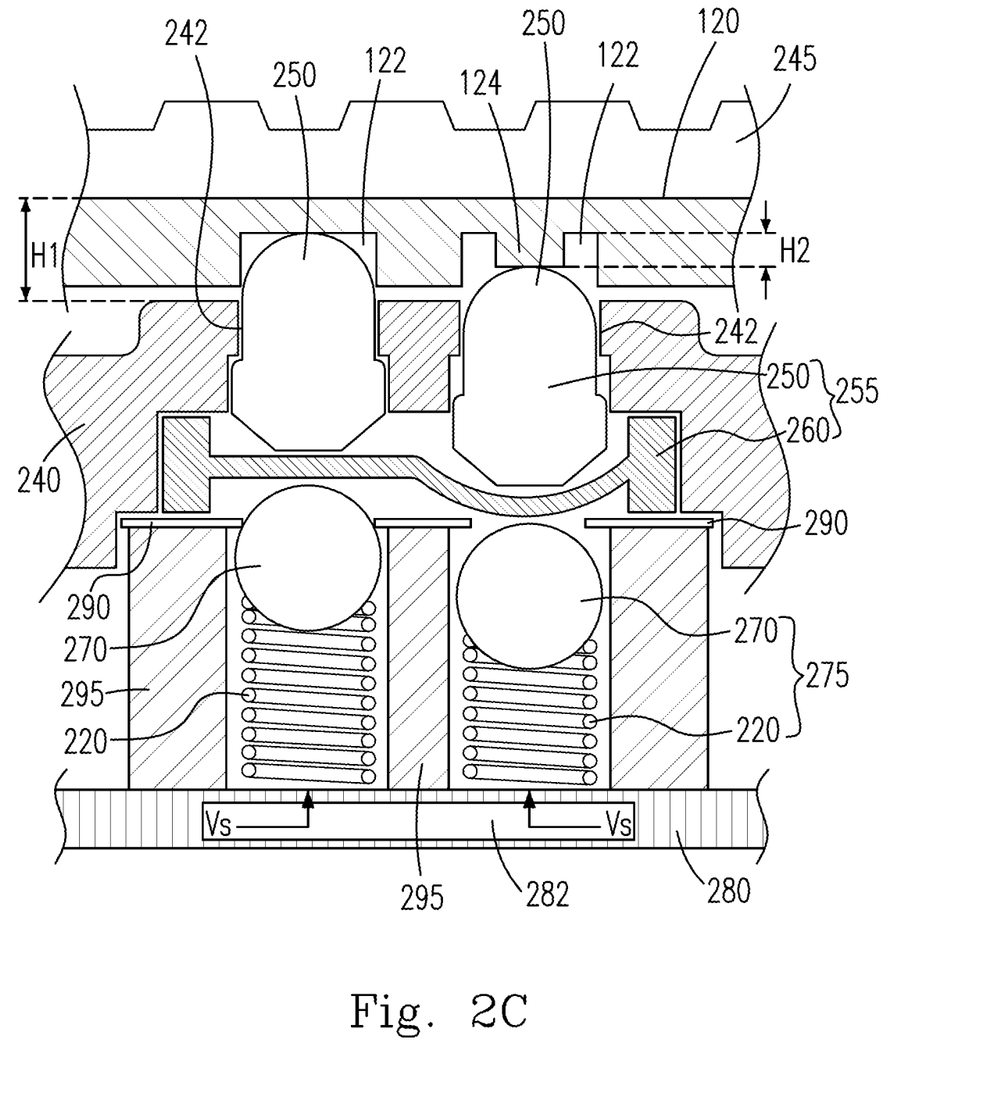

Referring to FIGS. 2B and 2C, which show sectional views of the test strip reader module 200 illustrated in FIG. 2A when the strip 120 is inserted therein. The test strip reader module 200 comprises the module main body 240 including the upper cover 245. As shown in FIG. 2B, the module main body 240 and the upper cover 245 are formed integrally. An upper strip contacting surface 212 and a lower strip contacting surface 214 can be defined in the strip insertion slot 210. From a different point of view, a height H1 of the strip insertion slot 210 for accommodating the test strip 120 is defined by the upper strip contacting surface 212 and the lower strip contacting surface 214 which makes the height of strip insertion slot 210 can be controlled by a single element since the height is defined when the module main body 240 was formed. In one embodiment of the present invention, the height H1 of the strip insertion slot 210 can be defined as a standard thickness of the test strip 120 plus a tolerance ranging between 0.05 and 0.5 millimeters. For example, the height H1 ranges between 1.05 and 1.5 millimeters when the standard thickness of the test strip 120 is 1 millimeter.

The module main body 240 also includes a first operation movement assembly 255 having an actuating element 250 for contacting a coding recess 122 on the test strip 120 and a blocking element 260 disposed below the actuating element 250, and a second operation movement assembly 275 having a conductive element 270 disposed under the blocking element 260 and an elastic element 220 for pushing the conductive element 270 upward. It is appreciated that a set of the first and the second operation movement assemblies 255, 275 are contained in one of operation holes 242 of the module main body 240. Alternatively, in other embodiments, the first operation movement assembly 255 is disposed in one operation hole 242 while the second operation movement assembly 275 is accommodated in a supporting portion 295 of the module main body 240.

The elastic element 220 can be, but not limited to, a spring, a metal elastic sheet or a metal dome. The shape of the conductive element 270 can be, but is not limited to, a column or ball-like element. The material of the conductive element 270 can be a metal material such as steel. The blocking element 260 is made of an elastic material such as rubber or silicone.

According to FIGS. 2B and 2C, a grounding element 290 is disposed under the blocking element 260, and the circuit board 280 has a signal source 282 providing an electronic signal Vs. It can be understood by the skilled person in the art that, under one condition that the test strip 120 is not inserted into the strip insertion slot 210, the conductive element 270 contacts the grounding element 290 due to a push from the elastic element 220, and a conducting condition is formed when the conductive element 270 is in contact with the grounding element 290 so the electronic signal Vs from the signal source 282 can come all the way through a circuit via the conductive element 270 to the grounding element 290. A current may exist in the circuit if the electronic signal is a voltage. When the test strip 120 is inserted in the strip insertion slot 210, as shown in FIGS. 2B and 2C, the actuating element 250 is not pushed down if the actuating element 250 is located under the corresponding coding recess 122 without a protrusion portion 124. Consequently, the conducting condition occurs, which can be determined as a first encoding signal or a first read signal.

On the other hand, the actuating element 250 in the operation hole 242 is pushed down and the conductive element 270 is separated from the grounding element 290 if the actuating element 250 is located under the corresponding coding recess 122 having a protrusion portion 124. According to one embodiment, a height H2 of the protrusion portion 124 for pressing the actuation element 250 ranges between 0.4 and 0.8 millimeters. Consequently, a non-conducting condition is formed when the conductive element 270 is separated from the grounding element 290 and the electronic signal Vs from the signal source 282 cannot be transmitted to the grounding element 290, which can be determined as a second encoding signal or a second read signal. Therefore, the read signal for a coding recess 122 at the corresponding position of the operation hole 242 can be determined based on one of the conducting and the non-conducting conditions. One may decode or identify the coding of a single recess 122 on the test strip 120 based on whether the current is formed due to the electronic signal Vs from the signal source 282 in the circuit board 280. For instance in a binary coding system, one of the coding conditions can be zero while the other can be one, and vice versa.

Figure 2D:
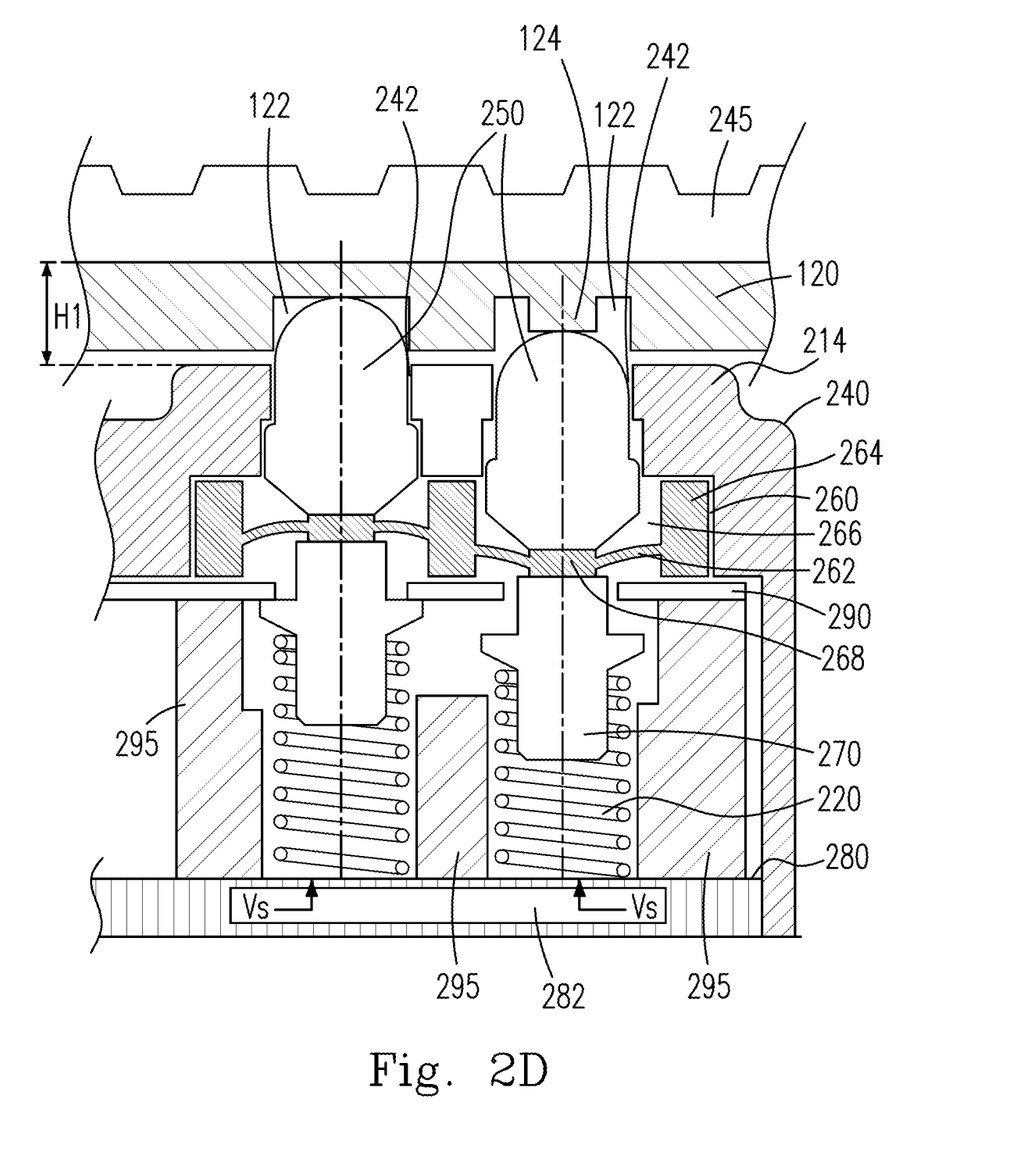
FIG. 2D is a schematic diagram showing a sectional view of the test strip reader module according to another embodiment of the present invention.

Please refer to FIG. 2D, which shows a sectional view of the test strip reader module according to another embodiment of the present invention. The operating concept for decoding the coding recesses 122 on the test strips 120 in FIG. 2D is similar to that of the embodiments illustrated in FIGS. 2B and 2C, and the difference is that each of the blocking elements 260 disposed in the operation holes 242 is operated independently. Deformation of a single blocking element 260 due to the vertical movement of the corresponding actuating element 250 in response to the coding in the coding recesses 122 will not cause any influence on the movement of the blocking elements 260 in different operation holes 242, so the issue of misreading due to the influence of the movement of adjacent actuating elements 250 may never exist. A protrusion 268 is formed in the blocking element 260 at a location corresponding to the actuating element 250, and may have a shape to match that of the actuating element 250, so additional pressure from the actuating element 250 toward the blocking element 260 is needed for allowing the actuating element 250 moving downward. In one embodiment, the portion of the conductive element 270 facing the blocking element 260 is flat. Consequently, the movement of conductive element 270 due to the compression of the blocking element 260 becomes more precise, and thus the judgment for the reading signal will be more accurate.

In this embodiment, the blocking element 260 includes a first blocker 262 having a cantilever shape and a second blocker 264 connected to the first blocker 262, and renders each of the actuating elements 250 disposed thereon can be moved independently without being effected by the movement in other operation holes 242 and causing a misread. In addition, first block 262 will deform when the blocking element 260 is compressed by the actuating element 250, and thus additional pressure from the actuating element 250 will be needed for pushing the conductive element 270 downward to achieve more accurate code reading. Furthermore, contamination such as a particle (not shown) can be collected into an L-shaped contamination collection portion 266 without effecting the electrical function down below when the contamination material accidently enters the test strip reader module 200 via the operation holes 242.

Figure 3:
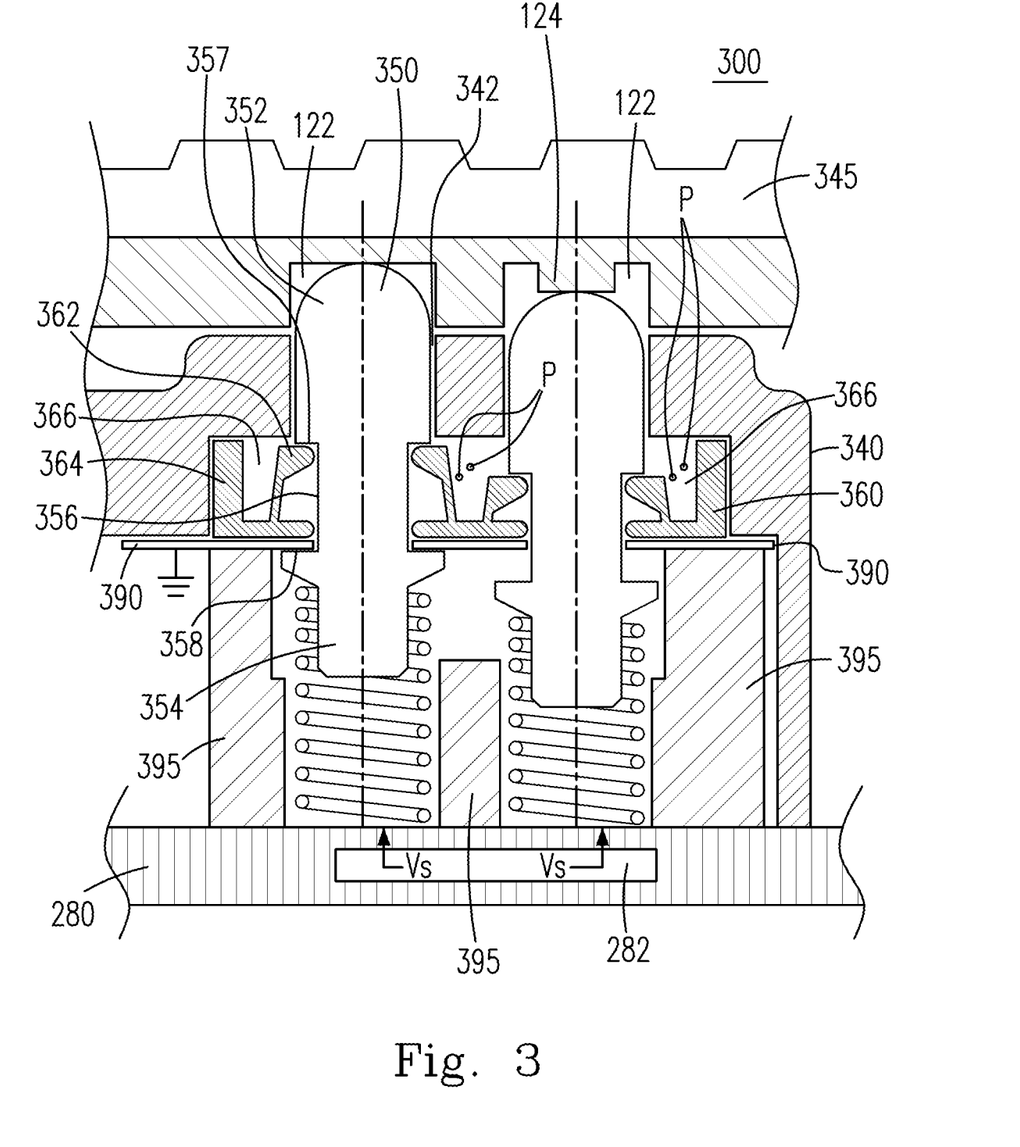
FIG. 3 is a schematic diagram showing a sectional view of the test strip reader module according to another embodiment of the present invention.

Please refer to FIG. 3, which shows a sectional view of the test strip reader module 300 when the test strip 120 is inserted into the strip insertion slot 210 according to another embodiment of the present invention, wherein the disposition of the elements such as the test strip 120, circuit board 280, the upper cover 345 and the main module body 340 are similar to those in the descriptions set forth above, and the differences are in that the actuating element is replaced by an elongated conductive element 350 having a first end 352 for contacting the coding recesses 122, a second end 354 for contacting the elastic element 220, a side groove 356 having a first groove wall 357 near the first end 352 and a second groove wall 358 disposed opposite to the first groove wall 357. The second end 354 and elastic element 220 are contained in the supporting portion 395. According to FIG. 3, the conductive element 350 at the left side faces the corresponding coding recess 122 without a protrusion, so the conductive element 350 at the left side is not compressed and the second groove wall 358 contacts the grounding element 390 to form a conducting status which can be identified as a first encoding signal, while the conductive element 350 at the right side faces to the corresponding coding recess 122 with a protrusion 124, so the conductive element 350 at the right side is compressed and moves downward and forms a separation status with the grounding element 390 which can be identified as a second encoding signal since the electronic signal Vs from the signal source 282 in the circuit board 280 cannot be transmitted to the grounding element 390 to generate a current. The blocking element 360 is preferably made of elastic material so it can be deformed along the vertical movement of the conductive element 350 while keeping a match condition with the first groove wall 357. The signal source 282 can include an ESD protection circuit for preventing the influence of electrostatic discharge caused by movement of the conductive element 350.

In addition to the dimensional variation due to element combination, the blocking elements may result in elastic fatigue and cause the test strip reader module operate abnormally. The present invention also provides solutions for avoiding the issue of contamination entering the inside of the reader module as described below.

Referring again to FIG. 3, in which the actuating element in FIGS. 2B-2D is replaced by the conductive element 350 having a cylinder-like shape while the operation holes 342 are sleeve-shaped, each of which contains one conductive element 350. The blocking element 360 includes a first side wall 362 matching the first groove wall 357 of the conductive element 350 and deforming along with the vertical movement of the conductive element 350. Therefore, the conductive element 350 can operate independently without being affected by the other conductive elements 350 in different operation holes 342. A contamination collecting device 366 is formed between the first side wall 362 and a second side wall 364, as illustrated in FIG. 3. When a contamination P such as overflow sample, quality control fluid, ash or particles accidentally enters the test strip reader module 300 from the operation holes 342, the contamination P will be contained in the contamination collecting device 366 without falling into the lower portion of the module main body 340 and affecting the electrical function thereof. It can be appreciated by the skilled person in the art based on FIG. 3 that the contamination collecting device 366 has a shape of a groove surrounding the side groove 356 of the conductive element 350.

Figure 4:
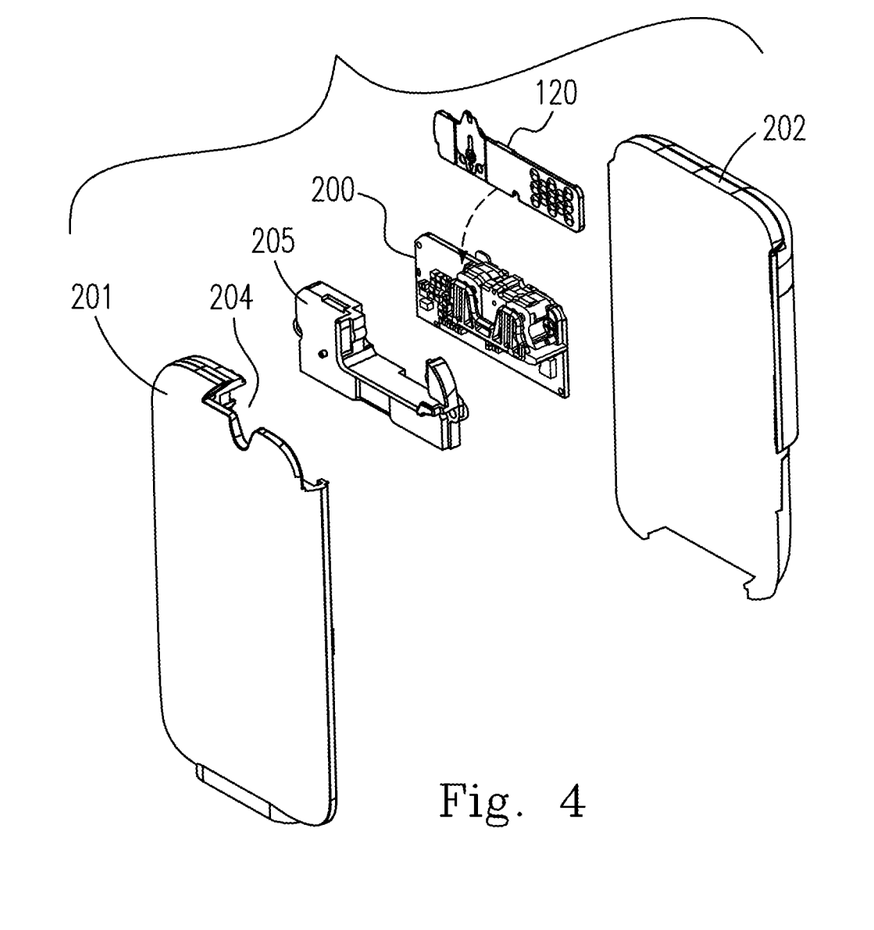
FIG. 4 is a perspective view showing how the test strip reader module is assembled into an electronic device, according to the present invention.

Please refer to FIG. 4, which shows how the test strip reader module 200/300 according to the present invention is assembled into an electronic device. The test strip reader module 200 itself has comprehensive functions for reading test strips, and can be connected to a communication module (not shown) disposed on a variety of mobile electronic devices such as cell phones, PDA or wearable electronic devices to allow the mobile electronic devices to analyze the analyte as well as transmitting the measurement data. The test strip reader module 200 can be adapted to the assembly accessory 205 to be disposed between the top cover 201 and the back over 202. The top cover 201 has an upper structure to accommodate the test strip reader module 200 and optionally shelter the upper cover 245 partly or wholly for modifying the front appearance of the electronic device while allowing the strip 120 to be easily inserted into the test strip reader module 200. In one embodiment of the present invention, the test strip reader module 200 has a thickness of about 12 millimeters which can be easily assembled. An electronic device furnished with the test strip reader module 200 can readily have all the functions of the test strip reader module 200.

Embodiments

1. A test strip reader, comprising: a module main body including an upper cover, a grounding element and at least one operation hole containing a first operation movement assembly and a second operation movement assembly; and a circuit board, wherein the upper cover and the module main body are formed integrally, and a condition of one of a contact status and a separation status between the second operation movement assembly and the grounding element determines a read signal.

2. The test strip reader in Embodiment 1, wherein the module main body further includes an upper strip contacting surface and a lower strip contacting surface to form a strip insertion slot integrally with the module main body for accommodating a test strip.

3. The test strip reader in Embodiment 2, wherein the strip insertion slot has a height being equal to a standard thickness of the test strip plus a tolerance ranging between 0.05 and 0.5 millimeters.

4. The test strip reader in Embodiment 2, wherein the test strip includes at least one protrusion having a protrusion height ranging between 0.4 and 0.8 millimeters.

5. The test strip reader in Embodiment 1, wherein the first operation movement assembly includes an actuating element for contacting at least one coding recess on the test strip.

6. The test strip reader in Embodiment 5, wherein the second operation movement assembly includes an elastic element.

7. The test strip reader in Embodiment 6, wherein the circuit board is disposed below the elastic element.

8. The test strip reader in Embodiment 5, wherein the first operation movement assembly further includes a blocking element disposed below the actuating element.

9. The test strip reader in Embodiment 6, wherein the second operation movement assembly includes a conductive element disposed under the blocking element and the elastic element for pushing the conductive element.

10. The test strip reader in Embodiment 9, wherein the conductive element contacts the grounding element due to a push from the elastic element, a conducting condition is formed when the conductive element is in contact with the grounding element, a non-conducting condition is formed when the conductive element is separated from the grounding element, and the read signal for a coding recess of a test strip at the corresponding position of the operation hole is determined based on one of the conducting and the non-conducting conditions.

11. The test strip reader in Embodiment 8, wherein the blocking element includes a contamination-collecting portion formed of a first sidewall and a second sidewall.

12. The test strip reader in Embodiment 11, wherein the blocking element further includes a protrusion matching with the actuating element.

13. A test strip reader, comprising: a module main body including an upper cover, a grounding element and at least one operation hole disposing therein a conducting element; and a circuit board, wherein the upper cover and the module main body are formed integrally, and a condition of one of a contact status and a separation status between the conducting element and the grounding element determines a read signal.

14. The test strip reader in Embodiment 13, wherein the conductive element includes a first end for contacting the test strip and a second end for contacting an elastic element.

15. The test strip reader in Embodiment 14, wherein the conductive element contacts the grounding element due to a push from the elastic element, a conducting condition is formed when the conductive element is in contact with the grounding element, a non-conducting condition is formed when the conductive element is separated from the grounding element, and the read signal for a coding recess of a test trip at the corresponding position of the operation hole is determined based on one of the conducting and the non-conducting conditions.

16. The test strip reader in Embodiment 14, wherein the conductive element further includes a side groove having a first groove wall near the first end and a second groove wall opposite to the first groove wall, and the second groove wall is configured to contact the grounding element in response to a push from the elastic element.

17. The test strip reader in Embodiment 16, further comprising a blocking element disposed at periphery of the side groove and matching with the first groove wall.

18. The test strip reader in Embodiment 17, wherein the second end is configured to be electrically connected to a signal source providing an electronic signal and having an ESD-protection circuit.

19. An electronic device for measuring an analyte, comprising:
 a test strip reader, including an upper strip contacting surface and a lower strip contacting surface;
 a top cover disposed above the test strip reader, and sheltering a top surface of test strip reader; and
 a back cover disposed below the test strip reader, and sheltering a bottom surface of test strip reader, wherein the upper strip contacting surface and the lower strip contacting surface form therebetween a space for accommodating a test strip, and the upper and lower strip contacting surfaces and the test strip reader are formed integrally.

20. The electronic device in Embodiment 19, wherein the test strip reader further includes a circuit board having a signal source providing an electronic signal.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A test strip reader, comprising:
 a module main body including an upper cover, a grounding element and at least one operation hole containing a first operation movement assembly and a second operation movement assembly, wherein the first operation movement assembly includes an actuating element for contacting at least one coding recess on the test strip and a blocking element disposed below the actuating element, and the second operation movement assembly includes an elastic element and a conductive element disposed under the blocking element and the elastic element for pushing the conductive element; and
 a circuit board,
wherein the upper cover and the module main body are formed integrally, a condition of one of a contact status between the second operation movement assembly and the grounding element and a separation status between the second operation movement assembly and the grounding element determines a read signal, the conductive element contacts the grounding element due to a push from the elastic element, a conducting condition is formed when the conductive element is in contact with the grounding element, a non-conducting condition is formed when the conductive element is separated from the grounding element, and the read signal for the at least one coding recess of the test strip at the corresponding position of the operation hole is determined based on one of the conducting and the non-conducting conditions.

2. The test strip reader as claimed in claim 1, wherein the module main body further includes an upper strip contacting surface and a lower strip contacting surface to form a strip insertion slot integrally with the module main body for accommodating a test strip.

3. The test strip reader as claimed in claim 2, wherein the strip insertion slot has a height being equal to a standard thickness of the test strip plus a tolerance ranging between 0.05 and 0.5 millimeters.

4. The test strip reader as claimed in claim 2, wherein the test strip includes at least one protrusion having a protrusion height ranging between 0.4 and 0.8 millimeters.

5. The test strip reader as claimed in claim 1, wherein the circuit board is disposed below the elastic element.

6. The test strip reader as claimed in claim 1, wherein the blocking element includes a contamination-collecting portion formed of a first sidewall and a second sidewall.

7. The test strip reader as claimed in claim 6, wherein the blocking element further includes a protrusion matching with the actuating element.

8. A test strip reader, comprising:
a module main body including an upper cover, a grounding element and at least one operation hole disposing therein a conducting element including a first end for contacting the test strip and a second end for contacting an elastic element; and
a circuit board,
wherein the upper cover and the module main body are formed integrally, a condition of one of a contact status between the conducting element and the grounding element and a separation status between the conducting element and the grounding element determines a read signal, the conductive element contacts the grounding element due to a push from the elastic element, a conducting condition is formed when the conductive element is in contact with the grounding element, a non-conducting condition is formed when the conductive element is separated from the grounding element, and the read signal for a coding recess of the test trip at the corresponding position of the operation hole is determined based on one of the conducting and the non-conducting conditions.

9. The test strip reader as claimed in claim 8, wherein the conductive element further includes a side groove having a first groove wall near the first end and a second groove wall opposite to the first groove wall, and the second groove wall is configured to contact the grounding element in response to the push from the elastic element.

10. The test strip reader as claimed in claim 9, further comprising a blocking element disposed at periphery of the side groove and matching with the first groove wall.

11. The test strip reader as claimed in claim 10, wherein the second end is configured to be electrically connected to a signal source providing an electronic signal and having an ESD-protection circuit.

12. An electronic device for measuring an analyte, comprising:
a test strip reader, including:
an upper strip contacting surface;
a grounding element;
at least one operation hole containing a first operation movement assembly and a second operation movement assembly, wherein the first operation movement assembly includes an actuating element for contacting at least one coding recess on a test strip and a blocking element disposed below the actuating element, and the second operation movement assembly includes an elastic element and a conductive element disposed under the blocking element and the elastic element for pushing the conductive element, and
a lower strip contacting surface,
a top cover disposed above the test strip reader; and
a back cover disposed below the test strip reader,
wherein the upper strip contacting surface and the lower strip contacting surface form therebetween a space for accommodating a test strip, the upper and lower strip contacting surfaces and the test strip reader are formed integrally, the conductive element contacts the grounding element due to a push from the elastic element, a conducting condition is formed when the conductive element is in contact with the grounding element, a non-conducting condition is formed when the conductive element is separated from the grounding element, and a read signal for the at least one coding recess of the test strip at the corresponding position of the operation hole is determined based on one of the conducting and the non-conducting conditions.

13. The electronic device as claimed in claim 12, wherein the test strip reader further includes a circuit board having a signal source providing an electronic signal.

* * * * *